United States Patent [19]

Pierschbacher et al.

[11] Patent Number: 5,700,681
[45] Date of Patent: Dec. 23, 1997

[54] SELECTION OF CELLS HAVING INCREASED CELL ADHESION PROPERTIES

[75] Inventors: Michael D. Pierschbacher; Erkki I. Ruoslahti, both of San Diego, Calif.; Shoukat Dedhar, North Vancouver, Canada

[73] Assignee: La Jolla Cancer Research Foundation, La Jolla, Calif.

[21] Appl. No.: 359,956

[22] Filed: Dec. 20, 1994

Related U.S. Application Data

[63] Continuation of Ser. No. 683,482, Apr. 9, 1991, abandoned, which is a continuation of Ser. No. 102,021, Sep. 28, 1987, abandoned.

[51] Int. Cl.$^6$ .............................. C12N 5/06; C07K 14/00
[52] U.S. Cl. .............................. 435/240.21; 435/240.2; 435/240.23; 530/350; 530/356
[58] Field of Search .................. 435/240.2, 240.21, 435/240.23, 948, 70.3, 375, 377; 530/350, 356

[56] References Cited

U.S. PATENT DOCUMENTS

| | | | |
|---|---|---|---|
| 4,565,789 | 1/1986 | Liotta et al. | 435/70.3 |
| 4,879,237 | 11/1989 | Rouslahti et al. | 435/240.2 |
| 4,988,621 | 1/1991 | Ruoslahti et al. | 435/240.2 |
| 5,049,659 | 9/1991 | Cantor et al. | 530/351 |
| 5,192,746 | 3/1993 | Lobl et al. | 514/11 |
| 5,238,839 | 8/1993 | Cantor et al. | 435/240.1 |
| 5,260,277 | 11/1993 | McKenzie | 544/18 |
| 5,436,221 | 7/1995 | Kitaguchi et al. | 514/12 |

OTHER PUBLICATIONS

Pierschbacher et al., Variants of the Cell Recognition Site of Fibronectin That Retain Attachment Promoting Activity. Proc. Natl. Acad. Sci. USA 81:5985–5988 (1984).

Pierschbacher et al., Synthetic Peptide with Cell Attachment Activity of Fibronectin. Proc. Natl. Acad. Sci. USA 80:1224–1227 (1983).

Pierschbacher et al., Cell Attachment Activity of Fibronectin Can Be Duplicated by Small Synthetic Fragments of the Molecule. Nature 309:30–33 (1984).

Pytela et al., Identification and Isolation of a 140 kd Cell Surface Glycoprotein with Properties Expected of a Fibronectin Receptor. Cell 40:191–198 (1985).

Ruoslahti et al., Alignment of Biologically Active Domains in the Fibronectin Molecules. J. Biol. Chem. 256:7277–7281 (1981).

Pierschbacher et al., The Cell Attachment Domain of Fibronectin. J. Biol. Chem. 257:9593–9595 (1982).

Hayman et al., Detachment of Cells from Culture Substrate by Soluble Fibronectin Peptides. J. Cell Biol. 100:1948–1954 (1985).

Cardarelli, P.M. et al., Proc. Natl. Acad. Sci., vol. 83(8), pp. 2647–2651, Apr. 1986.

Ekblom, P. et al., Proc. Natl. Acad. Sci., vol. 77(1), pp. 485–489, Jan. 1980.

Ruoslahti, E. et al., J. Cell. Biochem. Suppl., vol. 0(11, part B), p. 139. Abstract #1015, 1987.

Patel, V.P. et al., J. Cell. Biol., vol. 102(2), pp. 449–456, Feb. 1986.

Bronzert et al., "Selection and Characterization of a Breast Cancer Cell Line Resistant to the Antiestrogen LY 117018", Endocrinology V117, 1409–1417, 1985.

Hayman et al, "Detachment of Cells from Culture Substrate by Soluble Fibronectin Peptides", J. Cell Biol., V.100, 1948–1954, 1985.

Pierschbacher et al, "Location of the Cell Attachment Site in Fibronectin with Monoclonal Antibodies and Proteolytic Fragments of the Molecule", Cell, V.26 259–267, 1981.

Dedhar et al, "Human Osteosarcoma Cells Resistant to Detachment by an Arg–Gly–Asp–Containing Peptide Overproduce the Fibronectin Receptor," J. Cell Biol., V. 105, 1175–1182, 1987.

Pytela et al, "A 125/115–KDA Cell Surface Receptor Specific for Vitronectin Interacts with the Arginine–Glycine–Aspartic Acid Adhesion Sequence Derived from Fibronectin", PNAS, V. 82, 5766–5770, 1985.

Lash, J.W. et al., Developmental Biology, vol. 123(2), pp. 411–420, 1987.

Waite, K.A. et al., Experimental Cell Research, vol. 169(2), pp. 311–327, 1987.

*Primary Examiner*—Michael G. Wityshyn
*Assistant Examiner*—Kristin Larson
*Attorney, Agent, or Firm*—Campbell & Flores LLP

[57] ABSTRACT

A method for selecting cell lines expressing increased cell adhesion properties or promoting cell differentiation by culturing cells in increasing concentrations of adhesion ligand containing media. Cell lines produced by such method.

20 Claims, 1 Drawing Sheet

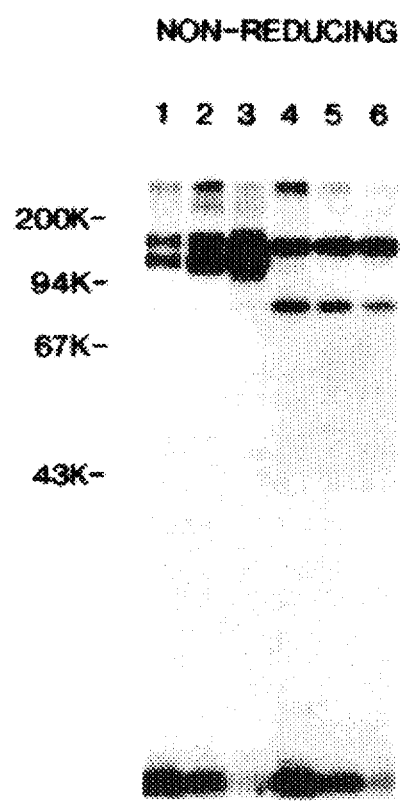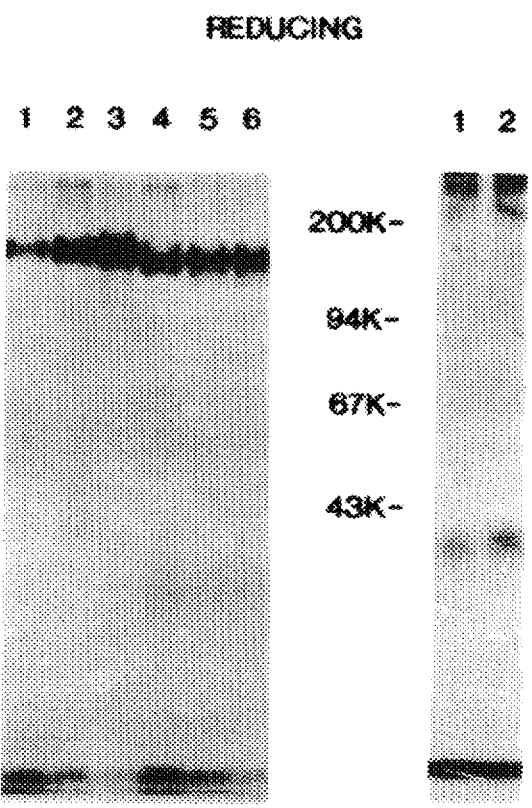
FIG. 1A  FIG. 1B  FIG. 1C

SELECTION OF CELLS HAVING INCREASED CELL ADHESION PROPERTIES

This application is a continuation of application Ser. No. 07/683,482, filed Apr. 9, 1991, now abandoned, which is a continuation of application Ser. No. 07/102,021, filed Sep. 28, 1987, now abandoned.

BACKGROUND OF THE INVENTION

This invention relates to cell adhesion systems, and more specifically to cells having increased cell adhesion properties.

The adhesion of cells to extracellular matrix components appears to be fundamental in cell behavior patterns such as cell division, cell differentiation, and embryonic cell migration and sorting. Moreover, certain abnormal cell behaviors, such as tumor invasion and metastasis, may result from alterations in the mechanisms of adhesion of cells to the extracellular matrix.

Cell adhesion appears to be mediated largely by cell surface receptors which recognize and specifically bind to cell adhesion-promoting molecules, or ligands, in the extracellular matrix. A number of such adhesion-promoting molecules have been identified including fibronectin, vitronectin, laminin and the collagens. It is now recognized that various of these adhesion-promoting molecules share the amino acid sequence arginine-glycine-aspartic acid (Arg-Gly-Asp or RGD) which functions as the cell-binding domain and accounts for the ability of cells to recognize and bind to these molecules.

Adhesive cells exhibit a number of different types of RGD-directed receptors on their surfaces, the proportion of which is specific to the cell type. Although these receptors all bind to the RGD-containing domain of their ligand, they nonetheless exhibit specificity to their particular cell-adhesion promoting molecule. Synthetic peptides containing the RGD sequence can be used to promote cell adhesion when coated on a substrate or to inhibit cell attachment when presented in soluble form.

Because the ability to bind to extracellular matrix components resides in the cell-surface receptors, the degree of cell adhesion should be affected by quantitative changes in the number of receptors present on the surface of the cells. A method to provide cell lines having enriched levels of receptors would be of considerable utility in providing cells which would exhibit increased binding ability and would provide a particularly useful source of cell surface receptors. Moreover, such a method may be useful for increasing the number of receptors in abnormal cell lines whose pathology results from a lowered number of receptors or in normal cell lines which have dedifferentiated as a result of a lowered number of receptors. The present invention satisfies these needs and provides related advantages as well.

SUMMARY OF THE INVENTION

The present invention provides a method for selecting for cells exhibiting increased adhesion properties by culturing cells from a parental cell line in media containing an adhesion ligand in solution in such concentration as to bind less than all adhesion surface receptors on the cells, and selecting those cells able to grow in such media for successive reculture in media containing increasing concentrations of the adhesion ligand in solution. The adhesion ligand in solution can be, for example, a peptide, such as one containing an RGD binding site, or an antibody, so as to inhibit the adhesion function of the adhesion receptors. Moreover, the invention provides an analagous method for promoting the differentiation of cells. Cell lines produced by such methods are also provided.

In an another aspect, the invention provides a further method for promoting the differentiation of cells in a cell line by selecting and reculturing those cells which express high levels of cell adhesion receptors on their surfaces. For example, the cells are exposed to a ligand specific to a cell adhesion receptor so as to permit binding between the ligand and the cells. The ligand may be either a binding partner of the adhesion receptor or an antibody which binds to the receptor, although not necessarily in such a way as to inhibit the receptors' binding function. Those cells having bound thereto the highest proportion of ligand are identified and selected for reculture in the presence of the ligand. The steps of culturing in the presence of the ligand, identification of those cells exhibiting high levels of bound ligand and reculture of these cells are repeated until the desired concentration of cell surface receptors and level of differentiation are established. One method of identifying such cells is through binding to a fluorescently labeled ligand and separating the cells by means of an automated cell sorter on the basis of the level of fluorescence expressed on their surfaces, although other methods well known in the art may be used alternatively.

BRIEF DESCRIPTION OF THE FIGURES

FIGS. 1A–1C. Immunoprecepitates of MG-63 and PRY cell surface antigens recognized by antibodies. MG-63 and PRY cells (about $10^5$) were surface-labeled with 1 mCi $^{125}$I, lysed, and the antigens immunoprecipitated as described in Example VI. Immunoprecipitates were analyzed by SDS-PAGE under nonreducing (FIG. 1A) or reducing (FIGS. 1B and 1C) conditions. (FIGS. 1A and 1B) Lanes 1–3, immunoprecipitation with antifibronectin receptor antibody; lanes 4, immunoprecipitation with antivitronectin receptor antibody; lanes 1 and 4, MG-63 cells (subconfluent culture); lanes 2 and 5, PRY cells (confluent culture); lanes 3 and 6, PRY cells (subconfluent culture). (FIG. 1C) Immunoprecipitation of subconfluent cultures of MG-63 (lane 1) and PRV (lane 2) cells with anti-HLA antibody.

DETAILED DESCRIPTION OF THE INVENTION

The invention relates to a method for providing cell lines having increased adhesion properties and increased states of differentiation by selecting cells able to grow in the presence of adhesion ligands in solution. RGD is the binding domain for a number of adhesion-promoting extracellular components such as fibronectin and vitronectin. Receptors on the surface of cells selectively bind to such adhesion promoting molecules.

To proliferate, normal cells must attach to a substrate. When an RGD-containing peptide is present in culture media, most cells fail to attach to, or detach from, an RGD-containing substrate. Thus, because most cells attach in culture via an RGD-dependent mechanism, in sufficient concentrations, generally above 1 mM, RGD inhibits cell proliferation in culture. This phenomenon has been extensively explored; see for example Hayman et al., J. Cell Biol. 100:1948, which is incorporated herein by reference. By an analagons mechanism, cell attachment can be inhibited other adhesion ligands or by antibodies which specifically bind to the adhesion receptor in question and interfere with the receptor's binding function.

The present invention provides a method of selecting for cells that have increased adhesive properties by exposing cell lines to successively increased concentrations of adhesion ligands in solution, for example an RGD peptide, and selecting and reculturing those cells which are able to attach and proliferate in such concentrations of the adhesion ligand. Such cells express increased numbers of adhesion receptors on their surfaces. Although the peptide GRGDSP has been used as the RGD-containing peptide as it is known to be recognized by a number of receptors, other RGD-containing peptides may be employed. Those known to have particular affinity to certain receptors may exert selective pressure to increase those particular receptors.

Many cells, including those of the MG-63 cell line, are known to attach to substrates in culture by secreting fibronectin, or a fibronectin-like substance, and attaching to the substrate thereto. RGD-containing peptide in solution in essence competes with the secreted fibronectin for binding to the fibronectin receptors, resulting in the described selective pressure placed on the cells for increased adhesive properties through, for example, the expression of increased numbers of fibronectin receptors. An analogous selective regime can be established by providing anti-fibronectin receptor antibodies in solution which will also compete with secreted fibronectin for binding to the fibronectin receptors and which will inhibit the adhesion function of the receptors.

Selective regimes to increase adhesion properties related to other RGD-specific cell surface receptors, or non-RGD-specific receptors, may also be utilized. For example, the culture substrate may be coated with an adhesion ligand such as vitronectin or a derivative thereof, and vitronectin or a vitronectin receptor-specific ligand or vitronectin receptor-specific antibody, provided in solution in such a concentration as to bind some, but not all, of the vitronectin receptors. Alternatively, the surface may itself be coated with a vitronectin receptor-specific antibody. In order to insure that the cells do not attach to the substrate through an alternative fibronectin-mediated mechanism, substantially all fibronectin receptors may be blocked by also presenting fibronectin receptor-specific ligands or antibodies in solution. Culture in successively increased concentrations of the vitronectin receptor-specific ligand or antibody result in increased adhesion properties of the cells related to the vitronectin specific cell surface receptors.

Alternatively, the substrate can be coated with a non-RGD-specific ligand or antibody to a non-RGD-specific receptor and a corresponding ligand or antibody provided in culture. The inherent mechanisms for cell attachment, such as that mediated by fibronectin secretion, can be blocked by the presence in appropriate quantities of an appropriate ligand or antibody appropriate to bind alternative adhesion receptors such as the fibronectin receptors.

Certain cells are known to secrete adhesion-promoting ligands other than fibronectin which are useful for mediating attachment of cells grown in culture. In such cell lines, increased adhesion properties related to these ligands and receptors may be promoted by culture in successive concentrations of the ligand secreted, a peptide analogue to the ligand or an antibody specific to the receptor corresponding to the ligand in question.

Analogous methods may be used to promote the differentiation of cells. While not wishing to be bound by such explanation, abnormal relatively undifferentiated malignant cells may exhibit reduced numbers of adhesion receptors on their surfaces. By selecting from such abnormal populations those cells exhibiting increased adhesive properties, cell differentiation is promoted. Useful cell lines having increased adhesive properties may thus be derived and such cell lines may have more differentiated properties. Moreover, normal undifferentiated stem cells may be forced into differentiating by being exposed to such a selective regime. Alternatively, cell lines which would be likely to dedifferentiate in cell culture can be maintained in a differentiated state by exposure to adhesion ligands in solution such as RGD-containing peptides.

The method may also be adapted for in vivo therapeutic use, such as to increase the number of adhesion cell surface receptors on, or the level of differentiation of, abnormal cells. For example, an adhesion ligand in solution may be introduced into an appropriate site in the body so as to contact the target cells. By binding to the adhesion cell surface receptors, the ligands may result in a disassociation of the target cells, or alternatively, may selectively promote the proliferation of cells having increasingly normal phenotypic expression of adhesion receptors and normal differentiated states.

The stepwise selection of cells, such as for example MG-63 human osteosarcoma cells, for attachment and growth in the presence of cell attachment-inhibiting concentrations of an adhesion ligand in solution, such as an RGD-containing peptide, for example, GRGDSP, results in the selection of cells capable of growing in the presence of the adhesion ligand in solution (such cells are hereinafter generally termed peptide resistant variant cells or PRV cells). These PRV cells overproduce cell surface receptors, such as that for fibronectin, as compared with the parental cells. In the case of a cell line derived from MG-63 cells, termed MG-63.3A, this overproduction is due to an increase in the levels of mRNA coding for the receptor. This increase is, however, not due to the amplification of the fibronectin receptor gene.

The PRV cells have retained the overproduction of the fibronectin receptor, the resistance of detachment from fibronectin-coated surfaces by the GRGDSP peptide, and the altered morphology for approximately 6 months during the last three of which they were grown in the absence of the GRGDSP peptide.

As used herein, the term "adhesion ligand" refers to any molecule which binds to a receptor whose function is to mediate cell adhesion. "Adhesion ligand" may include but is not limited to naturally occurring adhesion promoting chemical entities, derivatives thereof antibodies specific to adhesion cell surface receptors, or any other chemical entity capable of binding to adhesion related cell surface receptors.

Industrial Utility

By providing a method of promoting cell differentiation in culture, the invention permits obtaining and maintaining cultures capable of performing their differentiated functions. Such functional capability is important, for example, where cells having recombinant genomes are cultured in order to obtain secreted products. Further, fully differentiated and functional cells are necessary for certain transplantation uses, such is epithelial cells for skin transplants, endothelial cells for vascular grafts, secretory cells, such as insulin-secreting pancreatic cells for transplant into diabetic individuals and bone producing cells for bone replacement in culture. The method provides cells having increased adhesion properties, which are particularly suited for certain transplant operations, and may provide a ready source of receptors.

EXAMPLE I

SELECTION OF CELLS RESISTANT TO DETACHMENT BY RGD-CONTAINING PEPTIDE

The hexapeptide GRGDSP was synthesized using an automated peptide synthesizer and the chemistry provided by the manufacturer (Model 430A; Applied Biosystems, Foster City, Calif.). This peptide is known to bind to a variety of receptors through its RGD site.

The abbreviations used herein are as follows:
D—aspartic acid
E—glutamic acid
G—glycine
P—proline
R—arginine
S—serine Human osteosarcoma MG-63 cells were obtained from The American Type Culture Collection (Rockville, Md.). The cells were cultured in Dulbecco's modified Eagle's medium (DME), supplemented with 10% heat-activated fetal bovine serum (FBS) (Tissue Culture Biologicals, Tulare, Calif.), glutamine (2 mM), penicillin (100 U/ml), and streptomycin (100 µg/ml) (Irvine Scientific, Santa Ana, Calif.). For routine subculturing, cell monolayers were washed with phosphate buffered saline (PBS) (150 mM NaCl, 10 mM sodium phosphate, pH 7.3), and detached with EDTA (1 mM in PBS).

MG-63 cells were cultured in the presence of GRGDSP. The peptide was dissolved in DME and the pH was adjusted to 7.0 with sodium bicarbonate (7.5%). The solutions were then filter-sterilized before use.

When the hexapeptide GRGDSP was added to monolayer cultures of MG-63 cells at a concentration of 0.85 mM, the cells became detached from the substrate. The unattached cells (>99%) were removed and fresh medium containing the peptide (0.85 mM) was added to the remaining cells, some of which also detached from the substrate. These remaining few cells were incubated in the presence of the peptide and eventually a few cells were found to attach and spread. The cells were supplemented with fresh medium containing peptide and were found to be able to attach and grow under these conditions. Once confluent, the cells were detached with EDTA and subcultured in the presence of peptide. The concentration of the hexapeptide was subsequently increased from 0.85 to 5.0 mM in steps of 0.85 mM over a period of 5 months each time selecting for attached cells.

To address the question of the stability of the peptide for long periods in culture, spent medium from cells growing in the presence of the peptide for several days was applied to MG-63 cells not previously exposed to the peptide. These cells immediately detached from their culture substrates, indicating that the peptide was still active after several days in culture.

An MG-63 derived PRY cell line capable of attaching and spreading in the presence of 5.0 mM of GRGDSP peptide was termed MG-63.3A.

EXAMPLE II

SELECTION OF CELLS RESISTANT TO DETACHMENT BY ANTIBODIES SPECIFIC TO CELL ADHESION RECEPTORS

Antibodies specific to the fibronectin receptor and capable of inhibiting the adhesion function of the receptor were produced by the method of Example V and were further screened to determine that they inhibited the adhesion function of their corresponding receptors. Alternatively, monoclonal antibodies with similar properties can be produced by methods well-known in the art. The methodology of successively culturing cells of Example I is repeated, substituting fibronectin-receptor specific antibody for the RGD-containing peptide in solution. The initial concentration is selected to promote binding of the antibodies to less than all of the antibody specific receptors. Cells able to attach and survive in concentrations of the antibody sufficient to detach and kill cells of the parental line display increased adhesion properties.

EXAMPLE III

SELECTION OF CELLS RESISTANT TO DETACHMENT BY NON-FIBRONECTIN ADHESION PEPTIDES

Appropriate cells are selected for culture. If the cells are not capable of secreting a non-fibronectin adhesion promoting ligand by which the cells may attach to the substrate, the culture vessels are coated with an appropriate adhesion ligand. Alternatively, the substrate may be coated with an antibody reactive with the receptor of interest. If the cells are capable of spontaneously secreting a ligand corresponding to the receptor of interest, such coating is not necessary, but may nevertheless be performed.

The cells are grown in an initial medium containing an adhesion ligand in solution corresponding to the receptor of interest at a concentration selected so as to bind to less than all of the receptors of interest. Those cells which are able to attach and proliferate in this media are selected for reculturing in media containing successively increasing concentrations of the ligand of interest. Alternatively, antibodies to the receptor of interest may be provided in solution. In addition, an adhesion ligand (or antibody corresponding to the adhesion receptor) can be provided in solution in order to prevent cell attachment to the substrate through adhesion ligands secreted directly by the cells.

EXAMPLE IV

REPLICATES GROWN IN A NON-RGD PEPTIDE VARIANT

Replicate cultures were cultured in the presence of similar concentrations of a variant hexapeptide, GRGESP where E is glutamic acid, previously found to be inactive as a cell attachment-promoting agent and ineffective in detaching cells from their culture substrates (Hayman et al., (1985) J. Cell Biol. 100:1948). This GRGESP peptide did not have any effect on the MG-63 cells, which grew normally and were indistinguishable from MG-63 cells grown in the absence of this peptide.

EXAMPLE V

QUANTITATION OF FIBRONECTIN AND VITRONECTIN RECEPTORS BY FLOW CYTOMETRIC ANALYSIS

Fibronectin and vitronectin receptors on the cells were analyzed using affinity purified polyclonal antibodies reacting with these two receptors. The primary antibodies used were affinity-purified rabbit polyclonal anti-MG-63 vitronectin receptor and anti-MG-63 fibronectin receptor antibodies, rabbit anti-mouse epidermal growth factor receptor antiserum, and anti-HLA antibody. Fibronectin receptors and vitronectin receptors were isolated by the methods of Pytela et al., (1985) Cell 40:191 and Pytela et al., (1985) PNAS 82:5766, which are incorporated herein by reference. The antibodies were prepared by injecting rabbits with the appropriate immunogen using standard procedures. Absorbance of the resulting antiserum against normal human proteins resulted in the isolation of antibodies which were specific to either the fibronectin receptor or the vitronectin receptor.

The second antibody used was FITC-conjugated goat anti-rabbit IgG prepared by injecting goats with rabbit IgG by standard protocols and conjugating the antibodies to FITC by standard protocols. FITC fluorescence was detected as green fluorescence. Propidium iodide was used to label nonviable cells and detected as red fluorescence.

Cells were harvested with 1 mM EDTA and resuspended at a concentration of $2.5\times10^5$–$1\times10^6$ cells/ml in PBS containing 5% fetal calf serum (FCS) and 0.1% sodium azide. After washing the cells with the above buffer, 2 volumes (with respect to the cell pellet) of the respective antibody or antiserum were added. After incubation for 1 hour at 4° C., the cells were washed several times in the above buffer and FITC-conjugated goat anti-rabbit IgG was added to the cell suspension and incubated for 30 minutes at 4° C. After extensive washing, the cells were analyzed using a fluorescence-activated cell sorter (Ortho Cytofluorograf 50H). Cell preparations were stained by indirect immunofluorescence and analyzed using a fluorescence-activated cell sorter (Cytofluorograf 50H with 2150 computer system; Ortho Diagnostic Systems Inc., Westwood, Mass.).

Flow cytometric analysis of the two cell lines indicated that the PRV cells had a significant increase in the mean intensity of fluorescence as compared with the MG-63 cells when the fibronectin receptor was probed in indirect immunofluorescence, whereas no difference in the amount of staining of the vitronectin receptors was observed as compared with the MG-63 cells.

For comparison, a similar analysis carried out as above using anti-human leukocyte antigen (HLA) and anti-epidermal growth factor receptor antibodies showed no significant differences in the amount of these antigens present on the surfaces of these two cell lines. Determinations of cell sizes by forward and right-angle light scatter demonstrated that the cells had similar sizes in suspension, indicating that the increased staining with anti-fibronectin receptor antibodies indeed reflected the presence of increased amounts of receptor on the PRV cells.

EXAMPLE VI

QUANTITATION OF FIBRONECTIN RECEPTORS BY IMMUNOPRECIPITATION

The increase in the number of fibronectin receptors on the PRY cells was demonstrated by quantitative immunoprecipitation from $^{125}$I-surface-labelled cells followed by SDS-PAGE and autoradiography.

MG-63 and peptide-resistant variant cells were detached from culture with EDTA (1 mM) and resuspended with PBS containing $CaCl_2$ (1 mM) and $MgCl_2$ (1 mM). The cells (about $2\times10^6$) were surface-labeled with $^{125}$I as described in Pytela et al. (1985) Cell 40:191, which is incorporated herein by reference, and lysed in PBS containing SDS (0.1%), Triton X-100 (0.5%) (Sigma Chemical Co., St. Louis, Mo.), sodium deoxycholate (0.5%), and phenylmethylsulfonylfluoride (PMSF) (1 mM) for 15 min at 4° C. The solubilized cells were cleared of debris by centrifugation and cell extracts containing equivalent amounts of $^{125}$I radioactivity were immunoprecipitated with the appropriate antibodies by coprecipitation with protein A Sepharose. The antigen-antibody complex was dissociated by boiling in a sample buffer (200 m/4 Tris-HCl, pH 6.8 containing 3% SDS, 10% glycerol, and 0.001% bromophenol blue). Samples were analyzed by electrophoresis under reducing (5% 2-mercaptoethanol) or nonreducing conditions in 7.5% SDS-polyacrylamide gels followed by autoradiography, according to the method of Laemmli (1970) Nature 227:680.

The molecular weights of the proteins immunoprecipitated by the respective antibodies corresponded to the molecular weights of purified fibronectin and vitronectin and displayed the characteristic migration patterns on SDS polyacrylamide gels when subjected to electrophoresis under nonreducing and reducing conditions as described in Pytela et al., (1986) Science, 231:1559, which is incorporated herein by reference. The increase in the number of fibronectin receptors on PRV cells was quantitated by densitometric scanning of the autoradiographs, and the amount of each subunit was found to be approximately sixfold higher than on the parent line of MG-63 cells. A similar analysis of PRV cells growing in the absence of GRGDSP peptide demonstrated that these cells maintained this increase in fibronectin receptor numbers. The number of vitronectin receptors in the PRV cells appears to be similar to that of the MG-63 cells, consistent with the flow cytometric analysis of Example III.

For comparison, immunoprecipitation of Class 1 HLA antigen with anti-HLA antibodies did not show a significant difference in the amounts of this molecule between the two cell lines; these data were consistent in five separate experiments.

EXAMPLE VII

RNA DOT BLOT ANALYSIS

Total cellular RNA was prepared by the guanidinium/cesium chloride method of Ullrich et al. as described by Maniatis et al. (1982), Molecular Cloning, A Laboratory Manual, Cold Spring Harbor Laboratory, Cold Spring Harbor, N.Y., which is incorporated herein by reference. The RNA solution was adjusted to 20 mM sodium phosphate, pH 6.8, in 50% formamide (7% CV/V) formaldehyde and incubated at 65° C. for 15 minutes to denature the RNA. Dilutions were then made in 11×SSC (1×SSC is 0.15M NaCl, 1.5 mM sodium citrate) containing 37% formaldehyde and the RNA was applied to nitrocellulose filters that had been rinsed in 20×SSC. After baking at 80° C. for 2 hours in a vacuum oven, the filters were probed with [$^{32}$P]cDNAs as described below for the Southern blot analysis.

RNA dot blot analysis of total RNA from PRV and MG-63 cells using $^{32}$P-labeled cDNA for the fibronectin receptor α subunit indicated that the overproduction of the fibronectin receptor in the PRV cells correlated with a higher level of fibronectin receptor mRNA as compared with the MG-63 cells.

SDS-PAGE of [$^3$H]leucine- and $^{125}$I surface-labeled MG-63 and PRY cells failed to reveal any other major differences in the protein profiles of the two cell lines. Taken together, the above data suggest that the PRV cells express more fibronectin receptors than the parental MG-63 cells, and this difference appears to be due to a difference in the amount of mRNA for the fibronectin receptor in the two cells.

To determine whether gene amplification was the cause of the fibronectin receptor overproduction, high molecular weight DNA from MG-63 and PRV cells was digested with restriction endonucleases and analyzed by Southern blot analysis. For restriction enzyme analysis, the high molecular weight DNAs were isolated from cells by the procedures of Blin and Stafford (1976) Nucleic Acids Res., 3:2303. The restriction endonucleases were purchased from Bethesda Research Laboratories, Bethesda, Md. and were used according to the directions of the manufacturer. Digestion was followed by completion by mini-gel analysis. The digested DNAs were subjected to electrophoresis on 0.8% agarose gels in Tris/borate/EDTA buffer. After alkali denaturation and neutralization, the DNA was transferred to nitrocellulose paper. After baking the filter at 80° C. for 2 hours in a vacuum oven, the filter was prehybridized at 42° C. in a solution containing 50% formamide, 5×Denhardt's reagent, 5×SSPE (1×SSPE is 150 mM NaCl, 10 mM NaH$_2$PO$_4$, 1 mM EDTA), 0.1% SDS, and 100 µg/ml sheared and heat-denatured salmon sperm DNA. Hybridization was carried out at 42° C. for 16 hours in the above solution containing a $^{32}$P-oligolabeled fibronectin receptor α subunit cDNA consisting of a 675-bp Bam HI fragment from λP7 (Argraves et al. (1986) J. Biol. Chem. 261:12922) or $^{32}$P-oligolabeled vitronectin receptor α subunit cDNA consisting of a 1,283-bp fragment from λVNR10 (Suzuki et al. (1986) EMBO J 4:2519).

After hybridization, the filters were washed in 2×SSC, 1.5 mM sodium citrate, 0.1% SDS at room temperature for 1 hours followed by 1×SSC, 0.1% SDS at 65° C. for 1 hour. The filters were allowed to air dry and autoradiography was carried out at –70° C. using Kodak XAR-5 film and an intensifying screen (Cronex Lightning Plus, E.I. DuPont de Nemours, Newton, Conn.).

The hybridization signal for representative restriction enzyme digests of DNA isolated from both cell lines was of equivalent intensity when probed with cDNAs coding for the α subunits of the fibronectin receptor or the vitronectin receptor. The same results were obtained in separate experiments using other restriction enzymes. It therefore appears that the increased expression of the fibronectin receptor in the PRY cells was not due to gene amplification, but was probably due either to an increased rate of transcription of the fibronectin receptor gene or to increased stability of the receptor mRNA.

EXAMPLE VIII

ATTACHMENT TO FIBRONECTIN AND VITRONECTIN IN THE PRESENCE OF GRGDSP

If no qualitative change had taken place in the receptors, more peptide should be required to inhibit attachment to fibronectin of PRV cells than MG-63 cells, whereas similar concentrations of peptide would be required to inhibit attachment of either cell to vitronectin. Assays were carried using 96-well microtiter plates according to the method of Ruoslahti et al. (1982) Meth. Enz. 82:803, which is incorporated herein by reference. Two µg of fibronectin and 3 µg of vitronectin were used to coat each well, and 10,000 cells were provided per well.

The results are presented in Table I:

TABLE I

| | Concentration of peptide required for 50% inhibition of maximal cell attachment | |
|---|---|---|
| Substrate | MG-63 mM | PRV mM |
| Fibronectin | 0.21 | 5.30 |
| Vitronectin | 0.06 | 0.07 |

Maximum cell attachment in the absence of peptide: 60% for fibronectin and 80% for vitronectin.

Approximately 25-fold more peptide was required to achieve 50% inhibition of maximal attachment of PRV cells for fibronectin as compared with the MG-63 cells. However, virtually identical concentrations of peptide were effective at inhibiting attachment of either cell line to vitronectin. These data indicated that the peptide selection process has resulted in cells that adhere more tightly to fibronectin than do the parental cell line and they suggest that, in the presence of the peptide in culture, the PRV cells mainly use the fibronectin receptor, since the amount of peptide present in the selection medium clearly inhibits attachment to vitronectin but is not able to inhibit attachment to fibronectin.

EXAMPLE IX

CHARACTERIZATION OF PRV CELLS

The PRV cells displayed certain very different phenotypic properties from the MG-63 cell line including altered morphology, slower proliferation rate, ability to form a calcified matrix in vitro, increased synthesis of type I collagen, a 50–100 fold decrease in prostaglandin E synthesis and a decrease in chondroitin sulfate proteoglycan production. These characteristics indicate that the cells of the PRV line were more highly differentiated cell types than those of the MG-63 line. This cell line therefore resulted from the differentiation of a tumor cell line effected by the selective regime of Example I.

a. Morphology

The PRV cells were markedly different from the parental MG-63 cells, having a star-shaped morphology with multiple processes, some of which are many times longer than the cell bodies. These morphologic properties are not unlike those of osteocytes. The MG-63 cells, on the other hand, are essentially flat polygonal cells resembling fibroblasts. The PRY cells appeared to interweave and the cell processes were often seen to make connections with one another. In addition, the PRY cells appeared to be more secretory as judged by the granular nature of the cytoplasm and processes of these cells. PRV cells grown in the absence of GRGDSP peptide have maintained this morphology for at least 3 months, indicating that this morphologic alteration is a stable one. Karyotypic analysis of the two cell lines was carried out to ensure that they are related and also to determine whether any gross chromosomal changes had taken place in the PRV cells as compared with the MG-63 cells. Chromosomes from 5 MG-63 and 16 PRV cells were analyzed. These analyses showed that all of the cells examined from the two cell lines had in common nine distinguishable chromosome markers as well as trisomies of several of the chromosomes and the absence of a normal chromosome 9. These observations indicate that the PRV cells are indeed derived from the MG-63 cells. No obvious chromosomal changes indicative of gene amplification were observed in the PRV cells.

b. Growth Properties

The PRV cells have different growth properties from the MG-63 cells, proliferating at a much slower rate. They require some 15 days to reach confluency as compared with 4 days required by MG-63 cells when plated at the same initial density.

Tritiated thymidine incorporation analysis was performed. PRY and MG-63 cells were plated at equivalent cell densities in 96-well microtiter plates in the presence of 1 µCi thymidine methyl [$^3$H] (2.0 Ci/mmol). After incubation at 37° C. for various time periods, the cells were detached with 10 mM EDTA and harvested onto glass fiber cellulose discs using a cell harvester. The discs were allowed to dry and the radioactivity determined by liquid scintillation counting. Whereas MG-63 cells incorporated 82.397±13,000 cpm/10$^5$ cells per 24 hours, the PRY cells incorporated only 8,330±420 cpm/$10^5$ cells per 24 hours. (Results of two separate experiments, each experiment representing mean values of three measurements).

c. Calcified Matrix Formation

Cell monolayers were washed with PBS and stained for calcium deposits with Alizarin red S as described McGee-Russell, (1955) Nature 175:301. Briefly, the cells were fixed for 15 minutes in a 1:1 mixture of formaldehyde (37%) and absolute ethanol. The cell monolayers were brought to 50% ethanol and then rinsed rapidly with distilled water. The monolayers were covered with a 2% solution of Alizarin red S, pH 4.2. After 5 minutes, the cell monolayers were washed extensively with PBS to remove excess stain and reduce the background. Sites of calcium deposits could be observed as orange-red birefringent precipitates. The amount of stain associated with the cells was quantitated by solubilizing the cells in 0.1% SDS and measuring the absorbance at 465 nm in a spectrophotometer. Cell monolayers were also stained by the von Kossa silver test for calcium.

When confluent, PRY cells form many white nodules raised above the surface of the plastic culture dish that are clearly visible to the naked eye. These nodules stained positively for Alizarin red S, a dye which stains calcium deposits. MG-63 cells on the other hand grew as flat monolayers, did not form these nodules when confluent, and did not stain with Alizarin red S.

When observed under an inverted phase-contrast microscope, the nodules of the PRY cells appeared as refringent material which stained intensely with Alizarin red S. The intense staining of the nodules with Alizarin red S is not simply due to trapping of the dye since less confluent cultures of PRV also stained positively with Alizarin red S as compared to MG-63 cells. The quantity of stain associated with the PRV cells as determined spectroscopically increased with cell density while the value obtained for the PRY cells were essentially at backgound level. Similar cultures were also stained for calcium deposits by the von Koss silver stain. Staining by this method was positive only for the PRV cells with the pattern of distribution being the same as that of the Alizarin red S staining. That the areas staining intensely with these two dyes was not due to the presence of dead cells was determined by staining the cultures with the vital dye, Trypan blue. Most of the cells present in the areas staining with Alizarin red S and von Kossa stains excluded the Trypan blue, indicating that they were viable.

The presence of calcium phosphate in the nodules formed by the PRV cells was further demonstrated by energy dispersion X-ray analysis according to the method of Russ, (1971) Amer. Soc. for Testing and Materials, Special Public. 45. The data obtained by this technique clearly indicated the these PRV cell nodules contain a significantly greater amount of calcium phosphate than did similar size samples of MG-63 cells. The ratio of calcium to magnesium is approximately 10 for the PRV cells whereas it is close to 1.0 for MG-63 cells. Similarly, the ratio of phosphorous to sulphur is approximately 11 for the PRV cells and only 2 for MG-63 cells. However, ratios of other elements, such as sodium to aluminum are similar for both cell lines (1.25 for PRV cells and 1.4 for MG-63 cells). These data, coupled with $^{45}$Ca uptake studies showing that the PRY cells incorporated approximate 20-fold more calcium than the MG-63 cells during a 48 hour period, demonstrate the selective concentration of calcium phosphate in the nodules of the PRV cells.

d. Collagen Synthesis

The major types of collagens synthesized by MG-63 and PRV cells were analyzed. Briefly, cells were labeled for 24 hr with 50 µCi/ml of 5-[$^3$H] proline (9.3 Ci/mM) in DME containing 10% FCS and 100 µg/ml each of ascorbic acid and β-aminopropionitrite fumarate. The medium was made 0.5M with respect to acetic acid and the cells were dispersed in the medium containing 25 mM EDTA and 1 mM phenylmethylsulfonyl fluoride (PMSF). The cell suspension was sonicated for 30 seconds at 60 Hz and the insoluble residue removed by centrifugation. Aliquots containing equivalent amounts of protein from MG-63 and PRY cells were treated with 100 µg/ml of pepsin for 3 hours at 4° C. The pepsin digests were brought to pH 8.0 with NaOH and the types of collagen synthesized by the two cells lines analyzed by SDS-PAGE on 7.5% polyacrylamide gels as described above.

The fluorograms consistently showed two major bands co-migrating with standard $\alpha 1(I)$ and $\alpha 2(I)$ collagen chains synthesized by both cell lines, but the PRV cells synthesize approximately 5-fold more collagen type I. Therefore, it appears that although the major form of collagen synthesized by the MG-63 osteosarcoma cells is type I collagen, the PRV cells have upregulated the synthesis of this type of collagen, consistent with their more differentiated osteoblast-like phenotype and calcified matrix formation.

e. Prostaglandin Production

Because prostaglandins, especially PGE2, have been implicated in bone metabolism, the amount of $PGE_2$ synthesized and secreted by the MG-63 osteosarcoma cells and the PRV was quantitated by the specific radioimmunoassay procedure of Mitchell and Flint, (1978) J. Endrocrin. 76:111, which is incorporated herein by reference.

Radiolabeled products of $^{14}$C-arachidonic acid metabolism and unchanged substrate were separated by reverse phase HPLC using a $C_{18}$-$^5$µ Bondapak column (Waters, Milford, Mass.) as described previously according to the method of Mitchell et al., (1987), Prostaglandins, Leukotrines and Medicine 27:197, which is incorporated herein by reference.

As shown in Table 2, the amount of $PGE_2$ secreted by the MG-63 cells is approximately 50-fold higher than that secreted by the PRV cells in the presence of 10% fetal calf serum. The difference is even greater when the cells are grown under serum-free conditions. $^{14}$C-arachidonic acid metabolism by the two cell lines also demonstrated that the MG-63 cells metabolized a significantly greater percentage of arachidonic acid into prostaglandins as compared to the PRV cells (Table 3). Neither cell line metabolized the arachidonic acid by way of the lipoxygenase pathway to any detectable extent. These results suggest that there is a down-regulation of phospholipid metabolism in the PRV cells and tend to support the role of high levels of $PGE_2$ as a mediator of bone resorption rather than bone formation.

TABLE 2

Prostaglandin, PGE2 released into the culture medium by MG-63 and PRV

| | $PGE_2$ (pg/$10^6$ cells) | |
|---|---|---|
| | With Serum (10%) | Without Serum* |
| MG-63 | 4653 ± 510 | 2495 ± 800 |
| MG-63.3A | 118 ± 60 | 24 ± 15 |

*Cells were grown in defined medium which consisted of Dulbecco's minimum essential medium, F12 nutrient medium (Gibco) and transferrin/insulin/selenium mix (Collaborative Research Inc., Bedford, MA).

Values represent means from 3 separate experiments.

Cells were allowed to grow to approximately equivalent cell densities at which point the culture medium was removed and the level of $PGE_2$ determined by specific radioimmunoassay as described. The cells were removed from culture with 1 mM EDTA and cell numbers counted using an Artek cell counter.

TABLE 3

$^{14}$C-arachidonic acid metabolism into prostaglandins by MG-63 and PRV cells.

| | $^{14}$C-Prostaglandin Concentration (c.p.m./mg protein) | % of total labels metabolized to prostaglandins |
|---|---|---|
| MG-63 | 87,660 ± 1,700 | 18.0% |
| MG-63.3A | 4,642 ± 800 | 0.9% |

Values represent means of three separate experiments. Cells were cultured for 2 days in 2% fetal calf serum in the presence of $^{14}$C-arachidonic acid ($5 \times 10^5$ c.p.m.). Products of $^{14}$C-arachidonic acid metabolism were measured as described. Protein concentrations were determined by the method of Lowry et al.

f. Additional Features

One of the unique characteristics of the PRY cells is that they form clusters which grow and elaborate refringent material in which the cells are embedded. This material is rich in calcium phosphate. The light micrographic appearance of the calcified nodules formed by the PRV cells is very similar to that observed in primary osteoblast cultures from fetal rat calvaria, in osteoblast cultures form newborn mouse calvaria. The PRV cells, however, are able to carry out this mineralization in the absence of exogenous β-glycerophosphate, an essential requirement for matric mineralization in some primary osteoplast cultures, indicating that the PRY cells have activated biochemical pathways which are able to utilize the basal concentration of phosphate in the culture medium. Moreover, the PRV cells are non-malignant. When injected into nude mice, they fail to produce tumors, unlike the parental MG-63 cells which do produce tumors when so injected.

EXAMPLE X

REPLICATE CELL LINES

Two additional cell lines were exposed to the selective regime of Example I: SKNSH, a neuroblastoma, and HOS, an osteosarcoma, both on deposit with the American Type Culture Collection. After growth in media containing as much as 2 mg/ml GRGDSP, the HOS cell lines were found to overproduce receptors. The SKNSH line exhibited morphological changes after growth in media containing as much as 1.5 mg/ml of the RGD containing peptide. These results are consistent with the comparable changes toward increased adhesion and greater differentiation exhibited by the MG-63 cell lines at a comparable time in the selective regime.

Although the invention has been described with reference to the presently preferred embodiment, it will be appreciated that changes can be made without departing from the scope of the invention, which is limited only by the appended claims.

We claim:

1. A method for promoting differentiation of animal cells and preventing a differentiated state of animal cells from defifferentiating, comprising the steps of:
   a. providing an initial sample of said animal cells;
   b. culturing said animal cells in culture media containing an initial concentration of an RGD containing adhesion ligand in solution,
   wherein said RGD-containing adhesion ligand binds to RGD binding receptors on the surface of said animal cells which inhibits the adhesive function of said receptors, and wherein said initial concentration is selected so that not every receptor is bound;
   c. choosing those cells which proliferate in the presence of said initial concentration of said RGD containing adhesion ligand in solution;
   d. successively reculturing the chosen cells in culture media containing successively increasing concentrations of said adhesion ligand in solution;
   e. selecting those cells which proliferate in concentrations of said adhesion ligand in solution normally inhibitory to cell proliferation; and
   f. establishing from the selected cells a cell line which is more differentiated than said initial sample of animal cells.

2. The method of claim 1, wherein said RGD-containing adhesion ligand in solution is a peptide.

3. The method of claim 2, wherein said peptide is GRGDSP.

4. The method of claim 1, further comprising a step of coating the substrate of a vessel in which said initial sample of animal cells are cultured with an adhesion promoting material which binds to the same cell surface receptors as said RGD-containing adhesion ligand in solution.

5. The method of claim 1, further comprising:
   adding to the animal cell culture, to which said RGD containing adhesion ligand has been added, a receptor blocking molecule,
   wherein said receptor blocking molecule binds to cell surface receptors which do not bind said RGD-containing adhesion ligand.

6. The method of claim 5, wherein said receptor blocking molecule is provided in sufficient concentration to bind to about all of its corresponding cell surface receptor.

7. The method of claim 5 wherein said receptor blocking molecule will bind to fibronectin receptors.

8. The method of claim 1, wherein said initial sample of animal cells is selected from the group consisting of tumor cells, undifferentiated malignant cells, normal undifferentiated stem cells and dedifferentiated cells.

9. The method of claim 1, wherein said initial sample of animal cells are osteosarcoma cells.

10. The method of claim 1, wherein said initial sample of animal cells are MG-63 cells.

11. The method of claim 1, wherein said initial sample of animal cells are non-malignant cells.

12. A method for promoting the differentiation of animal cells and preventing a differentiated state of animal cells from dedifferentiating comprising the steps of:
   a. providing an initial sample of said animal cells;
   b. culturing said animal cells in culture media containing an initial concentration of an antibody in solution, wherein said antibody binds to RGD binding receptors on the surface of said animal cells which inhibits the adhesive function of said RGD binding receptors, and wherein said initial concentration is selected so that not every RGD binding receptor is bound;
   c. choosing those cells which proliferate in the presence of said initial concentration of said antibody in solution;
   d. successively reculturing said chosen cells in culture media containing successively increasing concentrations of said antibody in solution;
   e. selecting those cells which proliferate in concentrations of said antibody in solution normally inhibitory to cell proliferation; and
   f. establishing from said selected cells a cell line which is more differentiated than said initial sample of animal cells.

13. The method of claim 1 or 12, wherein said cell line of step (f) contains cells that do not proliferate or proliferate at a slower rate than animal cells in a less differentiated state.

14. A method of increasing the differentiated state of undifferentiated malignant animal cells, normal undifferentiated animal stem cells, and dedifferentiated animal cells, comprising the steps of:
   a) reacting a soluble RGD-containing adhesion ligand at an initial concentration with a sample of animal cells selected from the group consisting of undifferentiated malignant animal cells, normal undifferentiated animal stem cells, and dedifferentiated animal cells;
   b) permitting said RGD-containing adhesion ligand to specifically bind to RGD binding cell surface receptors on the animal cells;
   c) identifying the subset of animal cells which have bound the highest concentration of said RGD-containing adhesion ligand to their RGD binding cell surface receptors;
   d) isolating culturing said subset of animal cells in the presence of a concentration of said RGD-containing adhesion ligand that is higher than the concentration in step (a);
   e) collecting the animal cells from step (d) and reacting them with said RGD-containing adhesion ligand at a concentration equal to the concentration of RGD-containing adhesion ligand in step (d); and
   f) repeating steps (b) through (e) until the differentiated state of the animal cells isolated in step (d) is increased.

15. A method for promoting the differentiation of animal cells and maintaining a differentiated state of animal cells likely to dedifferentiate, comprising the steps of:
   a) providing a soluble RGD-remaining adhesion ligand at an initial concentration wherein said RGD-containing ligand binds selectively to RGD binding cell surface receptors expressed by animal cells;
   b) permitting said RGD-containing ligand to react with a sample of animal cells;
   c) identifying the animal cells which have bound the highest concentration of said RGD-containing adhesion ligand to their RGD binding cell surface receptors;
   d) isolating and culturing said animal cells identified in step (c) in the presence of a concentration of said RGD-containing adhesion ligand that is higher than the concentration in step (a);
   e) collecting the animal cells from the culture of step (d) and reacting them with said RGD-containing adhesion ligand at a concentration equal to the concentration of RGD-containing adhesion ligand in step (d); and
   f) repeating steps (b) through (e) until the desired differentiated state of the animal cells isolated in step (d) is obtained.

16. The method of claim 14 or 15, wherein said animal cells of step (f) do not proliferate or proliferate at a slower rate than animal cells in a less differentiated state.

17. The method of claim 1, 12, 14 or 15, wherein said animal cells are insulin-secreting pancreatic cells.

18. The method of claim 1, 12, 14 or 15, wherein said animal cells are bone producing cells.

19. The method of claim 1, 12, 14 or 15, wherein said animal cells in a differentiated state have increased adhesive properties.

20. The method of claims 14 or 15, further comprising:
   establishing from animal cells in step (f) a cell line which is more differentiated than said sample of animal cells.

* * * * *

UNITED STATES PATENT AND TRADEMARK OFFICE
CERTIFICATE OF CORRECTION

Page 1 of 4

PATENT NO. : 5,700,681
DATED : Dec. 23, 1997
INVENTOR(S) : Pierschbacher et al.

It is certified that error appears in the above-identified patent and that said Letters Patent is hereby corrected as shown below:

In column 2, line 28, please delete "PRY" and replace therefor with --PRV--.

In column 2, line 30, please delete "PRY" and replace therefor with --PRV--.

In column 2, line 38, please delete "PRY" and replace therefor with --PRV--.

In column 2, line 39, please delete "PRY" and replace therefor with --PRV--.

In column 2, line 62, please delete "analagons" and replace therefor with --analagous--.

In column 2, line 62, please insert --by-- between "inhibited" and "other".

In column 7, line 46, please delete "PRY" and replace therefor with --PRV--.

UNITED STATES PATENT AND TRADEMARK OFFICE
CERTIFICATE OF CORRECTION

PATENT NO. : 5,700,681
DATED : Dec. 23, 1997
INVENTOR(S) : Pierschbacher et al.

It is certified that error appears in the above-identified patent and that said Letters Patent is hereby corrected as shown below:

In column 7, line 62, please delete "m/4" and replace therefor with --mM--.

In column 8, line 47, please delete "PRY" and replace therefor with --PRV--.

In column 9, line 28, please delete "PRY" and replace therefor with --PRV--.

In column 10, line 32, please delete "PRY" and replace therefor with --PRV--.

In column 10, line 34, please delete "PRY" and replace therefor with --PRV--.

In column 10, line 60, please delete "PRY" and replace therefor with --PRV--.

In column 11, line 1, please delete "PRY" and replace therefor with --PRV--.

In column 11, line 7, please delete "described McGee" and replace therefor with --described in McGee--.

UNITED STATES PATENT AND TRADEMARK OFFICE
CERTIFICATE OF CORRECTION

Page 3 of 4

PATENT NO. : 5,700,681
DATED : Dec. 23, 1997
INVENTOR(S) : Pierschbacher et al.

It is certified that error appears in the above-identified patent and that said Letters Patent is hereby corrected as shown below:

In column 11, line 22, please delete "PRY" and replace therefor with --PRV--.

In column 11, line 30, please delete "PRY" and replace therefor with --PRV--.

In column 11, line 53, please delete "the" and replace therefor with --that--.

In column 11, line 63, please delete "PRY" and replace therefor with --PRV--.

In column 11, line 64, please delete "approximate" and replace therefor with --approximately--.

In column 12, line 15, please delete "PRY" and replace therefor with --PRV--.

In column 12, line 37, please delete "PGE2" and replace therefor with --$PGE_2$--.

In column 13, Table 2 heading, please delete "PGE2" and replace therefor with --$PGE_2$--.

UNITED STATES PATENT AND TRADEMARK OFFICE
CERTIFICATE OF CORRECTION

PATENT NO. : 5,700,681
DATED : Dec. 23, 1997
INVENTOR(S) : Pierschbacher et al.

It is certified that error appears in the above-identified patent and that said Letters Patent is hereby corrected as shown below:

In column 13, line 41, please delete "PRY" and replace therefor with --PRV--.

In column 13, line 52, please delete "PRY" and replace therefor with --PRV--.

Signed and Sealed this

Ninth Day of March, 1999

Attest:

Attesting Officer

Q. TODD DICKINSON

Acting Commissioner of Patents and Trademarks